United States Patent [19]

Cha

[11] Patent Number: 4,588,529

[45] Date of Patent: May 13, 1986

[54] MERCURY REMOVAL PROCESS

[75] Inventor: Dae Y. Cha, Kalamazoo, Mich.

[73] Assignee: The Upjohn Company, Kalamazoo, Mich.

[21] Appl. No.: 706,586

[22] Filed: Feb. 28, 1985

[51] Int. Cl.$^4$ .............................................. C07J 5/00
[52] U.S. Cl. .............................. 260/397.4; 260/397.45
[58] Field of Search ......................... 260/397.4, 397.45

[56] References Cited

U.S. PATENT DOCUMENTS

| | | | |
|---|---|---|---|
| 3,516,991 | 6/1970 | Walker | 260/239.5 |
| 3,629,298 | 12/1971 | Van Rheenen | 260/397.1 |
| 3,741,997 | 6/1973 | Berndt et al. | 260/397.4 |
| 3,764,615 | 10/1973 | Hausser | 260/397.4 |
| 4,102,908 | 7/1978 | Hofmeister et al. | 260/397.4 |
| 4,368,160 | 1/1983 | Mezel et al. | 260/397.4 |
| 4,443,377 | 4/1984 | Van Rheenen | 260/397.4 |

OTHER PUBLICATIONS

Helv. Chim. Acta. 26, 680 (1943), pp. 680–686.
Bach, Robert D. et al, "Sterochemistry of the Acetoxymercuration of Alkynes. A Synthesis of Vinyl Acetates", J. Org. Chem. 1982, 47, pp. 3707–3712.
Nussbaum, A. L. et al, "Enol Ethers of Steroidal $\Delta^4$–3–Ketones", J. Org. Chem. 26, (1961), pp. 3925–3928.
Steroid Reactions, edited by Carl Djerassi, Holden–Day, San Francisco, 1963, pp. 11–14; 42–45; and 49–53.

Primary Examiner—Elbert L. Roberts
Attorney, Agent, or Firm—William G. Jameson

[57] ABSTRACT

Oxymercuration reaction products (I) and/or mercury contaminated steroids (I) are purified by dissolving the compound in a suitable solvent and contacting with a metal dust selected from zinc, copper or iron and a suitable acid.

15 Claims, No Drawings

MERCURY REMOVAL PROCESS

DESCRIPTION

BACKGROUND OF THE INVENTION

Oxymercuration of ethisterone derivatives is old, see Helv. Chim. Acta. 26, 680 (1943).

The use of mercury salts as catalysts for enhancing the formation of the pregnane side chain on 17α-ethynyl steroids is well known. See, for example, U.S. Pat. Nos. 4,368,160, 4,102,908, 3,764,615, 3,741,997, and 4,443,377. See also U.S. patent application Ser. No. 501,032, filed 6/03/83.

In addition, the oxymercuration of epi-ethisterone and other 17β-ethynyl steroids is disclosed in U.S. patent application Ser. No. 673,961, filed Nov. 21, 1984.

The reaction of vinyl mercury acetates with zinc powder in glacial acetic acid to replace the mercuric acetate group with a proton is disclosed in "Stereochemistry of the Acetoxymercuration of Alkynes. Synthesis of Vinyl Acetates", J. Org. Chem. 1982, 47, 3707–3712.

SUMMARY OF THE INVENTION

Disclosed is a process for the removal of mercury from steroids, including mercury contaminated steroids and/or oxymercuration reaction products (II), which comprises dissolving the steroid in a suitable solvent and adding a metal powder or dust along with a small amount of a suitable acid to form an amalgam.

DETAILED DESCRIPTION OF THE INVENTION

The oxymercuration reaction products (II) of a 17-ethynyl steroid are well known to those skilled in the art. See, for example, U.S. Pat. Nos. 4,368,160, 4,102,908, 3,764,615, 3,741,997, 4,443,377 and U.S. patent application Ser. No. 501,032 filed June 3, 1983 and Ser. No. 673,961, filed Nov. 21, 1984.

The purification of 17α-acetyl-17β-hydroxy-16-methyleneandrost-4-en-3-one by stirring in a 2% acetic acid-methylene chloride mixture (0.3 g/ml) with zinc dust (5%) for 2–3 hours at 25° is disclosed in copending U.S. patent application Ser. No. 501,032, filed June 3, 1983.

The presence of detectable levels of mercury contamination in a steroid utilized in the synthesis of pregnane compounds used in the production of pharmaceuticals is undesirable.

The D-ring of a steroid, including the D-ring of the oxymercuration reaction product (II), can be combined with various combinations of A, B and C rings (see Chart B) and is represented by Formula I.

The oxymercuration reaction product (II) includes the standard (II') and the epi (II'') configuration.

The oxymercuration reaction product (II A-C) may or may not have the functionality at $C_3$ protected during the oxymercuration reaction (see Chart B). For the $\Delta^4$-3-keto steroids (A) the $C_3$ ketone is protected as the enol ether (Aa), ketal (Ab), enamine (Ac) or enol ester as is well known in the art, see Chart C. $R_3$ is alkyl of 1 thru 5 carbon atoms, with the proviso that for the ketal (b) its $R_3$'s can be connected. The preferred enol ether (Aa) is the methyl or ethyl ether. The preferred ketal (Ab) is the ethylene ketal. For the enamine (Ac) $R_3'$ and $R_3''$ are alkyl of 1 thru 5 carbon atoms; $R_3'$ and $R_3''$ may be the same or different and the $R_3'$ and $R_3''$ can be connected. The preferred enamines are selected from the group consisting of pyrrolidine, morpholine and diethylamino amines. The enol ethers (a) are prepared by methods well known in the art, see J. Org. Chem. 26, 3925 (1961), Steroid Reactions, edited by Carl Djerassi, Holden-Day, San Francisco 1963, page 42–45, and U.S. Pat. No. 3,516,991 (Preparation 1). The ketals (b) are also prepared by well known methods, see Steroid Reactions, supra, pages 11–14. The 3-enamines (c) are also prepared by methods well known in the art, see U.S. Pat. No. 3,629,298 and Steroid Reactions, supra, pages 49–53.

The $\Delta^{1,4}$-3-keto steroids (B) do not have to have the $C_3$ ketone protected. The 3-hydroxy steroid (C) may have the 3β-hydroxyl group protected as the ether (Ca) or ester (Cb), see Chart C. The preferred blocking groups are the methyl and ethyl enol ethers (Aa), ethylene ketal (Ab), pyrrolidine enamine (Ac), methyl ether (Ca) and acetate ester (Cb).

The $C_3$ protected forms (Aa, Ab and Ac) of the $\Delta^4$-3-keto steroids (A) an its $C_3$ protected forms (Ca and Cb) of the 3β-hydroxy steroids (C) are considered equivalent to the non-protected or free form (A and C) respectively, since the $C_3$ protecting groups are readily removable to convert the $C_3$ protected forms (Aa, Ab, Ca and Cb) to A and C, respectively.

Various substitutions at $C_6$, $C_9$ and $C_{11}$ are well known to the art. $R_6$ can be in either the α or β configuration and is a hydrogen, methyl, methylene, chlorine, fluorine or bromine atom. $R_9$ is alpha and can be nothing or a hydrogen, chlorine, fluorine or a bromine or oxygen atom, which includes the $\Delta^{9(11)}$ when $R_9$ is nothing and 9β,11β-epoxide functionality when $R_9$ and $R_{11}$ taken together are an oxygen atom. $R_{11}$ is a hydrogen, hydroxy, chlorine, bromine, fluorine or oxygen atom, which includes $\Delta^{9(11)}$ when $R_{11}$ is a hydrogen atom and the 9β,11β-epoxide functionality when $R_9$ and $R_{11}$ taken together are an oxygen atom and between $C_{11}$ and $R_{11}$ is a single bond. $R_{10}$ is a hydrogen atom or methyl group.

is a single or double bond and ~ indicates that the attached group can be in either the α or β configuration. X is a hydrogen atom or nothing.

≈ indicates that the attached group at $R_{16}$ is a single bond and in α or β configuration when $R_{16}$ is methyl or a double bond when $R_{16}$ is methylene; or at $R_6$ is a single bond and in α or β configuration except when $R_6$ is methylene when a double bond is present.

The oxymercuration reaction product (II) and $C_3$-protected forms thereof, as well as any mercury contaminated steroid (II) and $C_3$ protected forms thereof is dissolved in a suitable organic solvent and (1) a metal powder selected from the group consisting of zinc, copper or iron, preferably zinc and (2) a suitable acid, added. Suitable organic solvents include DMF, chlorinated organic solvents (e.g. methylene chloride), or acetone, preferably methylene chloride. A suitable organic or mineral acid such as sulfuric, hydrochloric or aliphatic (1 to 4 carbon atoms) carboxylic acid, preferably acetic is added so as to activate the metal powder.

The term metal powder, also known as metal dust, refers to metal particles of zinc, copper or iron of about 841 microns to about 5 microns, preferably less than about 44 microns.

Illustrative oxymercuration reaction products (II) include:

17α-acetyl-17β-hydroxy-16-methyleneandrost-4-en-3-one;

17β-acetyl-17α-hydroxy-16-methyleneandrost-4-en-3-one;
17α-acetyl-17β-hydroxy-6,16-dimethyleneandrost-4-en-3-one;
17α-formyloxy-19-nor-4-pregnene-3,20-dione;
17α-formyloxy-18-methyl-19-nor-4-pregnene-3,20-dione;
17α-acetoxy-4-pregnene-3,20-dione;
17α-methoxy-19-nor-4-pregnene-3,20-dione;
17α-formyloxy-pregna-1,4-diene-3,20-dione;

The process is preferably carried out at about 25° C. but a temperature range of about 0° C. to the boiling point of the solvent can be utilized. A quantity of solvent sufficient to totally dissolve the steroid is preferred. An amount of metal powder sufficient to complex any mercury present and/or to form a mercury-metal amalgam, i.e. at least 0.01 gm of metal per 1.0 gm of steroid; is added, with agitation, to the solution at about pH 0 to 5 pH, preferably 2 to 5.

After stirring for 0.2 to 5 hours, the suspension is filtered, and the filtrate concentrated and the product recovered according to methods well known to those skilled in the art. Prior to filtration, bicarbonate sodium can optionally be added if desired.

If desired, the process of the subject application may be repeated a number of times (preferably 3 or more) for a particular sample to further reduce the level of mercury. In general, the second crop obtained from the mother liquor of the first crystallization should be combined with the next crude lot product or purified according to the subject process before combining with the first crop since the second crop will usually have a higher mercury content.

The preferred process of the subject invention (zinc powder/glacial acetic acid/methylene chloride) can be repeated a sufficient number of times to reduce the level of mercury for a particular sample to 5 ppm or less.

DEFINITIONS

The definitions and explanations below are for the terms as used throughout the entire patent application including both the specification and claims.

All temperatures are in degrees Centigrade.
TLC refers to thin-layer chromatography.
THF refers to tetrahydrofuran.
Saline refers to an aqueous saturated sodium chloride solution.
NMR refers to nuclear (proton) magnetic resonance spectroscopy, chemical shifts are reported in ppm (δ) downfield from TMS.
TMS refers to tetramethylsilane.
When solvent pairs are used, the ratios of solvents used are volume/volume (v/v).
ppm refers to parts per million.
DCPS refers to directly coupled plasma emission spectroscopy.
MAGNESOL refers to magnesium silicate.
CELITE refers to a brand of diatomaceous earth filter aid from Johns-Manville.
DMF refers to N,N-Dimethylformamide.

EXAMPLES

Without further elaboration, it is believed that one skilled in the art can, using the preceeding description, practice the present invention to its fullest extent. The following detailed examples describe how to perform the process of the invention and are to be construed as merely illustrative, and not limitations of the preceeding disclosure in any way whatsoever. Those skilled in the art will promptly recognize appropriate variations from the procedures both as to reactants as well as to reaction conditions and techniques.

Preparation 1

Synthesis of 16-methylene-17β-hydroxyepiprogesterone, 17α-acetyl-17β-hydroxy-16-methyleneandrost-4-en-3-one.

A mixture of mercuric oxide (4.6 mmole) dissolved in sulfuric acid (1.3M, 38 ml) is added to a slurry of 17α-ethinyl-17β-hydroxy-16-methyleneandrost-4-en-3-one in acetone (300 ml) under a nitrogen atmosphere. The mixture is heated at 50° overnight and then cooled to 20°–25°. The mixture is neutralized with sodium bicarbonate, filtered through CELITE. Acetone and water are added. Upon workup a crude product is obtained. The crude material is crystallized from acetone to give the title compound.

EXAMPLE 1

Zinc Powder Process

Twenty grams of 16-methylene-17β-hydroxyepiprogesterone prepared in accordance with Preparation 1 and containing 248 ppm mercury as assayed by DCPS is dissolved in 150 ml of methylene chloride. To the solution, 1.0 gram of zinc powder (Standard Zinc Dust-122, the New Jersey Zinc Co.—through a 325 mesh screen), followed by 1 ml of glacial acetic acid, is added at room temperature and stirred for two hours with a magnetic stirrer.

2 gm MAGNESOL and 3 gm CELITE are added, the mixture stirred, and filtered over a 10 gm MAGNESOL precoat. The filter cake is washed with a small volume of methylene chloride.

Combined filtrate and wash solution are concentrated under vacuum to about 100 ml and the resulting concentrate is mixed with 200 ml acetone to commence precipitation. Further concentration of the mixture to about 100 ml residual volume results in a thick slurry. The slurry is filtered and the cake washed with acetone and dried in a vacuum oven at 50° C. to obtain 15 gm of 16-methylene-17β-hydroxyepiprogesterone which contains less than 5 ppm (by DCPS) mercury. The sensitivity is increased later to ~1 ppm.

EXAMPLE 2

Copper Powder Process

Twenty grams of 16-methylene-17β-hydroxyepiprogesterone prepared in accordance with Preparation 1 and containing 248 ppm mercury by DCPS is dissolved in 150 ml of methylene chloride. To the solution, 1.0 gram of copper powder (Glidden Metals 500RL), followed by 1 ml of glacial acetic acid, is added at room temperature and stirred for two hours with a magnetic stirrer.

2 gm MAGNESOL and 3 gm CELITE are added, the mixture stirred, and filtered over a 10 gm MAGNESOL precoat. The filter cake is washed with a small volume of methylene chloride.

Combined filtrate and wash solution are concentrated under vacuum to about 100 ml and the resulting concentrate is mixed with 200 ml acetone to commence precipitation. Further concentration of the mixture to about 100 ml residual volume results in a thick slurry. The slurry is filtered and the cake washed with acetone and dried in a vacuum oven at 50° C. to obtain 14.7 grams of 16-methylene-17β-hydroxyepiprogesterone which contains less than 13 ppm of mercury by DCPS.

EXAMPLE 3

Iron Powder Process

Twenty grams of 16-methylene-17β-hydroxyepiprogesterone prepared in accordance with Preparation 1 and containing 248 ppm mercury by DCPS is dissolved in 150 ml of methylene chloride. To the solution, 1.0 gram of iron powder (Fine Iron M-1, Iron Specialties Co.), followed by 1 ml of glacial acetic acid, is added at room temperature and stirred for two hours with a magnetic stirrer.

2 gm MAGNESOL and 3 gm CELITE are added, the mixture stirred, and filtered over a 10 gm MAGNESOL precoat. The filter cake is washed with a small volume of methylene chloride.

Combined filtrate and wash solution are concentrated under vacuum to about 100 ml and the resulting concentrate is mixed with 200 ml acetone to commence precipitation. Further concentration of the mixture to about 100 ml residual volume results in a thick slurry. The slurry is filtered and the cake washed with acetone and dried in a vacuum oven at 50° C. to obtain 15.4 grams of 16-methylene-17β-hydroxyepiprogesterone which contains less than 11.4 ppm of mercury.

EXAMPLE 4

A two liter round bottom flask is charged with 60 grams of 17α-ethynyl-17β-hydroxy-16-methylene-androst-4-en-3-one (16-methylene-ethisterone) and 600 ml of acetone; and 2.0 grams of red mercuric oxide dissolved in a solution of 70 ml of water and 4.9 ml of concentrated sulfuric acid is added all at once and the mixture heated to 50° C. and stirred until the reaction is complete, as monitored by TLC. To the reaction mixture, 24 grams of hydrated sodium acetate is added to neutralize the sulfuric acid and the mixture stirred to prepare a solution of about pH 4. As the product begins to precipitate, 600 ml of acetone is added, followed by 10 grams of zinc dust (powder) with stirring at 50° C., the stirring continued for several hours or overnight.

A mixture of 10 grams MAGNESOL and 15 grams CELITE is added to the slurry and stirred for 10 minutes. The slurry is then filtered over a layer made with a mixture of 15 gm MAGNESOL and 10 gm CELITE at the bottom and additional MAGNESOL at the top. The filter cake is washed with a mixture of 100 ml water and 100 ml methanol, followed by 100 ml of methanol. The combined filtrate and methanol wash is transferred into a 1 liter (3 neck) round bottom flask and concentrated under vacuum to about 700 ml, cooled to 15° C. and filtered. The filter cake is washed with a mixture of 100 ml water and 100 ml acetone followed by a small volume (about 25 ml) of acetone. The filter cake is dried in a vacuum oven at 60° C. for 2 hours to yield 16-methylene-17β-hydroxyepiprogesterone.

Hg=89 ppm.

EXAMPLE 5

Multi-Step Zinc Process

Part I

Combine 10.0 Kg of 16-methylene-17β-hydroxyepiprogesterone (Preparation 1) and 0.5 Kg of zinc powder in a reactor vessel, flush with nitrogen until the oxygen content is less than 4%, then 26 liters methylene is chloride added and the mixture stirred at room temperature to dissolve the steroid. 350 ml of glacial acetic acid is added and stirred for two hours at about 25° C. 0.883 Kg of sodium bicarbonate is added to the reaction mixture as a dry powder, washed down with methylene chloride and stirred for 15 min. at room temperature. The slurry is filtered through a pot filter precoated with at least one inch of MAGNESOL/methylene chloride. The reactor vessel is rinsed and the filter cake washed with methylene chloride. The combined filtrate is reduced by distillation to about 20 liters residual volume under atmospheric pressure, the reactor cooled and 50.0 liters (39.3 Kg) of acetone added to the concentrate. Continue concentration under atmospheric pressure to a thick slurry. Cool and add 50.0 liters of acetone to the slurry and concentrate again under atmospheric pressure to complete displacement of solvent. Cool the slurry to about 0° C. and stir for 15–20 minutes, filter the slurry using a small pot filter. The cold reactor is rinsed with 5 Kg of acetone and the filter cake washed with the cold acetone, followed by a 10 Kg and 5 Kg wash with acetone. The filter cake is dried to a constant weight in a vacuum oven at 50° C. to obtain the first crop of the product 16-methylene-17β-hydroxyepiprogesterone (weight of product in Kg=A). The mother liquor is concentrated under vacuum at below 50° C. to obtain a thick slurry, cooled and filtered. The reactor vessel is rinsed and the filter cake washed with cold acetone. The filter cake is dried to a constant weight in a vacuum oven at 50° C. to obtain a second crop of the product.

Part II

Combine the first crop of the 16-methylene-17β-hydroxyepiprogesterone (Ex. 5, Part I) and, (A×0.05) Kg of zinc powder in a reactor vessel, flush with nitrogen until the oxygen content is less than 4%, then add (A×3.5) liters of methylene chloride and stir to dissolve. (A×35) ml of glacial acetic acid is added and the mixture stirred for two hours at 25° C. (A×0.0883) Kg of sodium bicarbonate is added to the reaction mixture as a dry powder, washed down with methylene chloride and stirred for 15 min. at room temperature. The slurry is filtered through a pot filter, precoated with at least one inch of MAGNESOL/methylene chloride. The reactor vessel is rinsed and the filter cake washed with of methylene chloride. The combined filtrate is reduced by distillation to about (A×3.0) liters residual volume under atmospheric pressure, the reactor is cooled and (A×5) liters of acetone is added to the concentrate. Continue concentration under atmospheric pressure to a thick slurry. Cool and add (A×5) liters of acetone. The solution is concentrated under reduced pressure to complete displacement of the solvents. Cool the slurry to about 0° and stir for 15–20 min. Filter the slurry using three clean medium frit filters. Each cake is washed twice with 500 ml of cold acetone. The filter cake is dried to a constant weight in a vacuum oven at 50° to obtain the first crop of the product 16-methylene-17β-hydroxyepiprogesterone (weight of product in Kg=B).

The mother liquor is transferred to a 12-liter flask, the reactor vessel rinsed with acetone and added to the mother liquor, concentrated under vacuum at below 50° to obtain a thick slurry, which is cooled and filtered. The flask is rinsed and the filter cake washed twice with 250 ml of cold acetone. The filter cake is dried to a constant weight in a vacuum oven at 50° to obtain a second crop of the product.

Part III

Combine 16-methylene-17β-hydroxyepiprogesterone from the first crop of Part II and (B×0.05) Kg of zinc powder in a reactor vessel, flush with nitrogen until the oxygen content is less than 4%, then add (B×3.5) liters of methylene chloride and stir to dissolve. (B×35) ml of glacial acetic acid is added and the mixture stirred for 2 hours at about 25° C. (B×0.0883) Kg of sodium bicarbonate is added to the reaction mixture as a dry powder, washed down with methylene chloride and stirred for 15 minutes at room temperature. The slurry is filtered through a pot filter precoated with at least one inch of MAGNESOL/methylene chloride. The reactor vessel is rinsed and the filter cake washed with methylene chloride. The combined filtrate is reduced by distillation to about (B×3.0) liters residual volume under atmospheric pressure, the organic product transferred to a 12 liter flask and distilled to about 4 liters under atmospheric pressure. The flask is cooled and (B×2.0) liters of acetone added to the concentrate. Continue concentration under atmospheric pressure to a thick slurry. Cool and add (B×2.0) liters of acetone to the slurry and concentrate again under atmospheric pressure to complete displacement of the solvent. Cool the slurry to about 0° C. and stir for 15 min., filter the slurry using a small pot filter. The cooled vessel is rinsed twice with 500 ml of acetone and the filter cake washed with the cold acetone. The filter cake is dried to a constant weight in a vacuum oven at 50° C. to obtain the first crop of the product 16-methylene-17β-hydroxyepiprogesterone (weight of product in Kg=C).

The mother liquor is concentrated under vacuum at below 50° to obtain a thick slurry, cooled and the slurry filtered. The vessel is rinsed and the filter cake washed with cold acetone. The filter cake is dried to a constant weight in a vacuum oven at 50° to obtain a second crop of the product.

Part IV

Combine 16-methylene-17β-hydroxyepiprogesterone from the first crop from Part III Example 5) and (C×0.5) gm of zinc powder in a reactor vessel, flush with nitrogen until the oxygen content is less than 4%, then add (C×35) liters methylene chloride in a flask, stir to dissolve the steroid. (C×3.5) ml of glacial acetic acid is added and the mixture stirred for two hours at about 25°. Add (C×0.883) gm of sodium bicarbonate to the reaction mixture as a dry powder, wash down with methylene chloride, and stir for 15 minutes. The slurry is filtered through a pot filter precoated with at least one inch of MAGNESOL/methylene chloride. The reactor vessel is rinsed and the filter cake washed with methylene chloride. The combined filtrate is transferred to a 5 liter 3-neck round bottomed flask and reduced to about (C×2) liters residual volume under atmospheric pressure, cool the flask and add (C×3) liters of acetone to the concentrate. Continue concentration under atmospheric pressure to a thick slurry. Cool and add (C×3) liters of acetone to the slurry and concentrate again under atmospheric pressure to complete displacement of the solvent. Cool the slurry to 0° and stir for 15 min., filter the slurry using a small pot filter. The cold vessel is rinsed with acetone and the filter cake washed with cold acetone. The filter cake is dried to a constant weight in a vacuum oven at 50° to obtain the first crop of the product 16-methylene-17β-hydroxyepiprogesterone.

EXAMPLE 6

Part I

Preparation of 17α-acetyl-17β-hydroxy-6,16-dimethyleneandrost-4-en-3-one.

9.0 Kg of 17α-ethynyl-17β-hydroxy-6,16-dimethyleneandrost-4-en-3-one is added to a reactor vessel, flushed with nitrogen until the oxygen content is less than 4%. 108 Liters (85.3 Kg) of acetone is added and the solution heated to 45° C. A catalyst solution (prepared by the addition of 0.72 liters conc. sulfuric acid to 10.8 liters of deionized water, followed by the addition of 576 grams of mercuric oxide, red powder to the dilute acid) is added to the reaction mixture and stirred at 45° C. until the reaction is complete, as monitored by TLC. The reaction mixture is cooled to less than 25° C. and 2.3 Kg Celite 545, 2.2 Kg sodium acetate and 20 liters of water added and mixture stirred for 15 min. The resulting crude product is filtered using a pot filter coated with Celite 545. The reactor is rinsed with 50 liters of acetone and filtered. The combined filtrate is concentrated under vacuum to about 50 liters, cooled to below 20° C. and stirred for 15 min. The slurry is filtered and the filter cake washed with 10 liters of acetone and 20 liters of water. The filter cake is dried in a vacuum oven at 50° C. to yield 17α-acetyl-17β-hydroxy-6,16-dimethyleneandrost-4-en-3-one (mercury content 10,500 ppm).

Part II

Zinc Process 7.3 Kg of 17α-acetyl-7β-hydroxy-6,16-dimethyleneandrost-5-en-3-one, prepared by the procedure of Part I, Example 6) and 0.365 Kg of zinc powder is combined in a reactor vessel, flushed with nitrogen until the oxygen content is less than 4%, then 26 liters of methylene chloride added and the mixture stirred at room temperature to dissolve the steroid. 255 ml of glacial acetic acid is added and the mixture stirred for 2 hours at 25°. 0.645 Kg of sodium bicarbonate is added to the reaction mixture as a dry powder, washed down with methylene chloride and stirred for 15 min at room temperature.

The slurry is filtered through a pot filter. The reactor vessel is rinsed and the filter cake washed with 36 liters of methylene chloride. The combined filtrate is reduced by distillation to about 15 liters residual volume under atmospheric pressure, the reactor cooled and 298 g (380 liters) of acetone added to the concentrate. Continue concentration under atmospheric pressure to a thick slurry. Cool again and add 30.5 Kg of acetone. The solution is concentrated under reduced pressure to complete displacement of the solvents. Cool the slurry to about −2° and stir for 20 min., filter the slurry using a small pot filter. The cooled vessel is rinsed with acetone and the filter cake washed with the cold acetone. The filter cake is dried to a constant weight in a vacuum oven at 50° to obtain the first crop of the product 6,16-dimethylene-17β-hydroxyepiprogesterone, with a mercury content of 179 ppm.

The mother liquor is concentrated under vacuum at below 50° to obtain a thick slurry, which is cooled and filtered. The flask is rinsed and the filter cake washed twice with 250 ml of cold acetone. The filter cake is dried to a constant weight in a vacuum oven at 50° to obtain a second crop of the product.
FORMULA
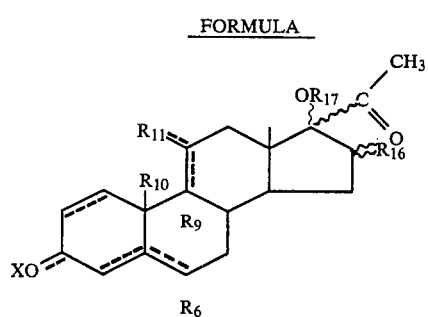
I
CHART A
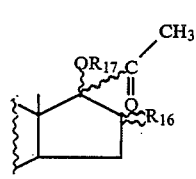
II
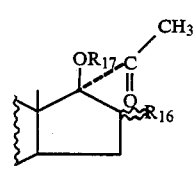
II'
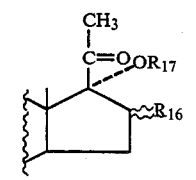
II"
CHART B
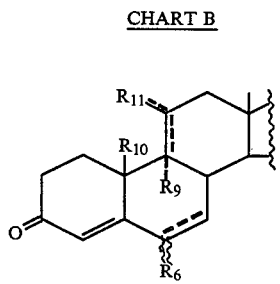
(A)
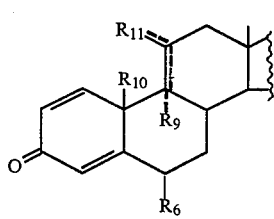
(B)
CHART B -continued
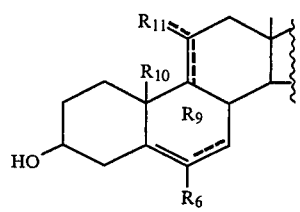
(C)
CHART C
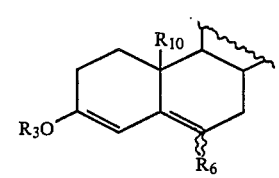
(Aa)
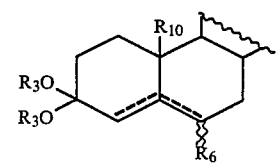
(Ab)
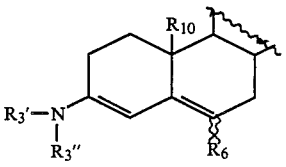
(Ac)
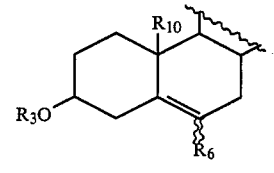
(Ca)
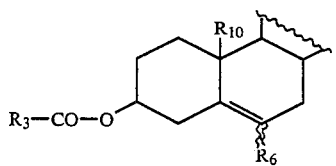
(Cb)
I claim:
1. A process for removing mercury from a mercury contaminated steroid of the formula

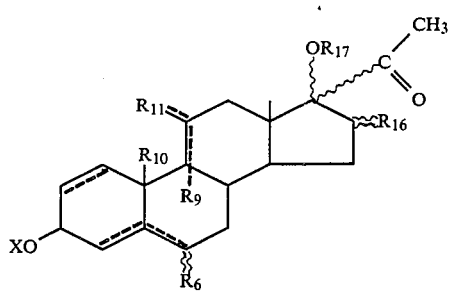

and C$_3$ protected forms thereof, where X is a hydrogen atom or nothing, when X is nothing, the ═ at C$_3$ is a double bond, when X is a hydrogen atom the ─ at C$_3$ is a single bond; R$_6$ is a hydrogen, chlorine, fluorine or bromine atom, methyl or methylene group; R$_9$ is nothing, a hydrogen, chlorine, fluorine, bromine or oxygen atom which makes the C-ring (a) $\Delta^{9(11)}$ when R$_9$ is nothing, (b) 9$\beta$,11$\beta$-epoxide when R$_9$ and R$_{11}$ taken together are oxygen atom;

R$_{10}$ is a hydrogen atom or methyl group; R$_{11}$ is a hydrogen, chlorine, bromine, fluorine or oxygen atom, two hydrogen atoms or $\alpha$- or $\beta$-hydroxyl group which makes the C-ring (a) $\Delta^{9(11)}$ when R$_{11}$ is a hydrogen atom, (b) 9$\beta$,11$\beta$-epoxide when R$_9$ and R$_{11}$ taken together are oxygen atom and ─ between C$_{11}$ and R$_{11}$ is a single bond;

R$_{16}$ is a hydrogen atom, methyl or methylene, an ≈ is an $\alpha$ or $\beta$ single bond when R$_{16}$ is methyl or a double bond when R$_{16}$ is methylene; R$_{17}$ is a hydrogen atom, methyl, ethyl, formyl or acetyl which comprises dissolving the product in a solvent selected from the group consisting of methylene chloride, acetone or DMF; adding (1) a metal powder selected from the group consisting of zinc, copper or iron and (2) an acid selected from the group consisting of aliphatic (C$_1$–C$_4$) carboxylic acid, sulfuric acid or hydrochloric acid; and removing the mercury-metal amalgam.

2. A process according to claim 1 where the mercury contaminated steroid is a compound of the formula

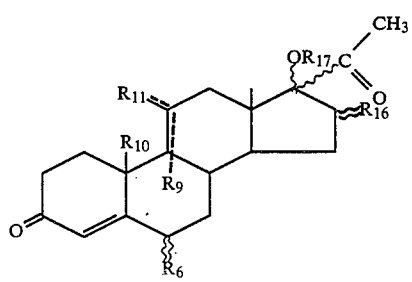

and C$_3$ protected forms thereof.

3. A process according to claim 1 where the mercury contaminated steroid is a compound of the formula

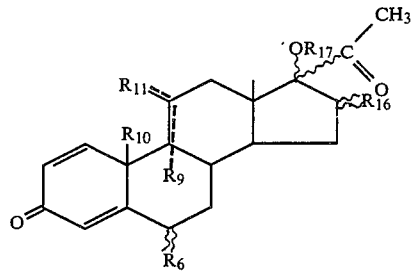

4. A process according to claim 1 where the mercury contaminated steroid is a compound selected from the group consisting of

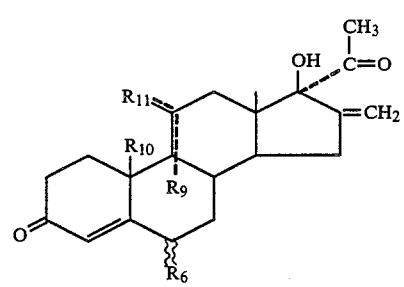

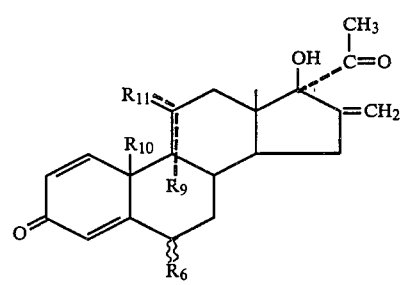

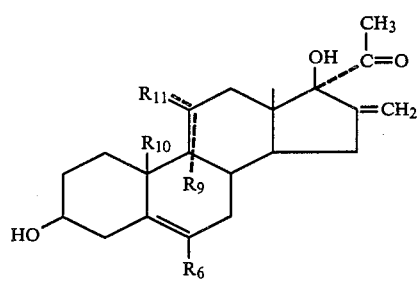

and C$_3$ protected forms thereof.

5. A process according to claim 1 where the mercury contaminated steroid is a compound selected from the group consisting of

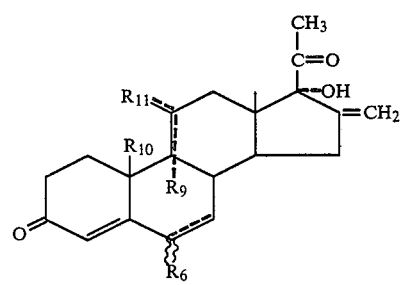

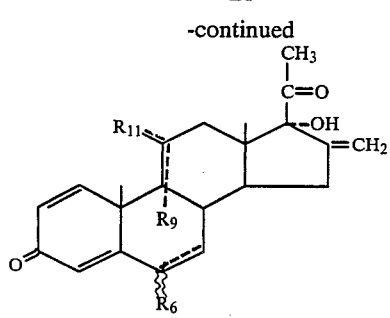

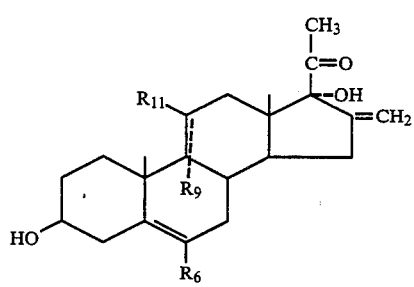

and C$_3$ protected forms thereof.

6. A process according to claim 4 where the solvent is methylene chloride.

7. A process according to claim 1 where the metal dust is zinc dust.

8. A process according to claim 1 where the acid is acetic acid.

9. A process according to claim 1 where the mercury contaminated steroid is selected from the group consisting of:

∫ α-acetyl-17β-hydroxy-16-methyleneandrost-4-en-3-one;

17β-acetyl-17α-hydroxy-16-methyleneandrost-4-en-3-one;

17α-acetyl-17β-hydroxy-6,16-dimethyleneandrost-4-en-3-one;

17α-formyloxy-19-nor-4-pregnene-3,20-dione;

17α-formyloxy-18-methyl-19-nor-4-pregnene-3,20-dione;

17α-acetoxy-4-pregnene-3,20-dione;

17α-methoxy-19-nor-4-pregnene-3,20-dione;

17α-formyloxy-pregna-1,4-diene-3,20-dione.

10. A process for removing mercury from a mercury contaminated compound of the formula

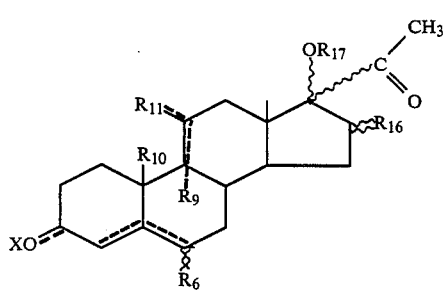

and C$_3$ protected forms thereof, where X is a hydrogen atom or nothing, when X is nothing, the   at C$_3$ is a double bond, when X is a hydrogen atom the   at C$_3$ is a single bond; R$_6$ is a hydrogen, chlorine, fluorine or bromine atom, methyl or methylene group; R$_9$ is nothing, a hydrogen, chlorine, fluorine, bromine or oxygen atom which makes the C-ring (a) $\Delta^{9(11)}$ when R$_9$ is nothing, (b) 9β,11β-epoxide when R$_9$ and R$_{11}$ taken together are oxygen atom;

R$_{10}$ is a hydrogen atom or methyl group; R$_{11}$ is a hydrogen, chlorine, bromine, fluorine or oxygen atom, two hydrogen atoms or α- or β-hydroxyl group which makes the C-ring (a) $\Delta^{9(11)}$ when R$_{11}$ is a hydrogen atom, (b) 9β,11β-epoxide when R$_9$ and R$_{11}$ taken together are oxygen atom and   between C$_{11}$ and R$_{11}$ is a single bond;

R$_{16}$ is a hydrogen atom, methyl or methylene, an ≈ is α or β when R$_{16}$ is methyl or a double bond when R$_{16}$ is methylene; R$_{17}$ is a hydrogen atom, methyl, ethyl, formyl or acetyl which comprises dissolving the product in methylene chloride; adding (1) zinc powder and (2) acetic acid and removing the mercury-metal amalgam.

11. A process according to claim 10 where the mercury contaminated steroid is a compound of the formula

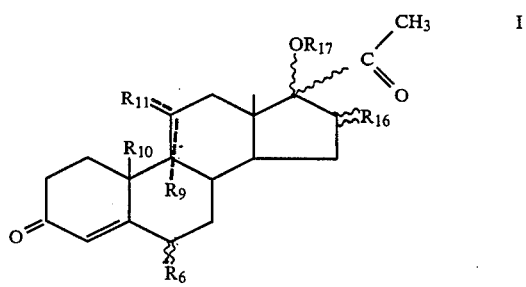

and C$_3$ protected forms thereof.

12. A process according to claim 10 where the mercury contaminated steroid is a compound of the formula

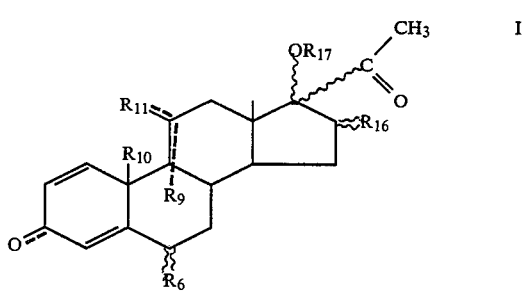

13. A process according to claim 10 where the mercury contaminated steroid is a compound selected from the group consisting of

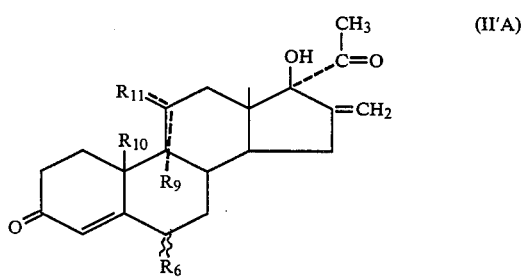

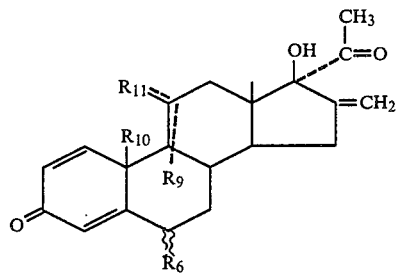

(II'B)

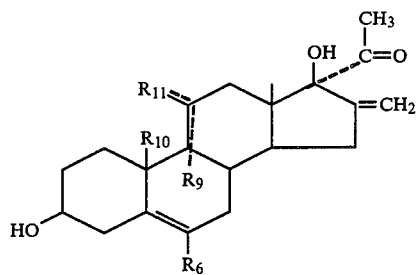

(II'C)

and C₃ protected forms thereof.

14. A process according to claim 10 where the mercury contamined steroid is a compound selected from the group consisting of

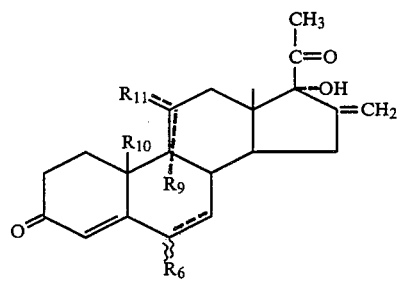

(II"A)

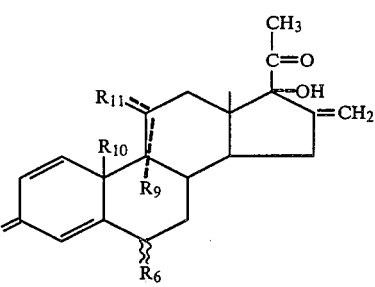

(II"B)

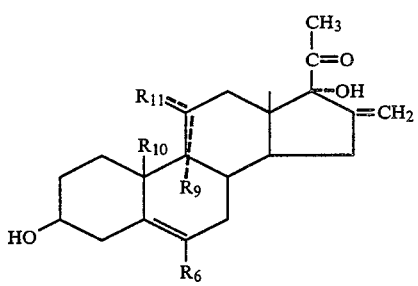

(II"C)

and C₃ protected forms thereof.

15. A process according to claim 10 where the mercury contaminated steroid is a compound selected from the group consisting of:
  17α-acetyl-17β-hydroxy-16-methyleneandrost-4-en-3-one;
  17β-acetyl-17α-hydroxy-16-methyleneandrost-4-en-3-one;
  17α-acetyl-17β-hydroxy-6,16-dimethyleneandrost-4-en-3-one;
  17α-formyloxy-19-nor-4-pregnene-3,20-dione;
  17α-formyloxy-18-methyl-19-nor-4-pregnene-3,20-dione;
  17α-acetoxy-4-pregnene-3,20-dione;
  17α-methoxy-19-nor-4-pregnene-3,20-dione;
  17α-formyloxy-pregna-1,4-diene-3,20-dione.

* * * * *